United States Patent
Lee et al.

(10) Patent No.: US 10,398,637 B2
(45) Date of Patent: Sep. 3, 2019

(54) COSMETIC COMPOSITIONS FOR TREATING KERATINOUS SUBSTRATES

(71) Applicant: L'OREAL, Paris (FR)

(72) Inventors: Heather Lee, Wayne, NJ (US); Angela Park, Jersey City, NJ (US)

(73) Assignee: L'OREAL, Paris (FR)

( * ) Notice: Subject to any disclaimer, the term of this patent is extended or adjusted under 35 U.S.C. 154(b) by 211 days.

(21) Appl. No.: 15/388,191

(22) Filed: Dec. 22, 2016

(65) Prior Publication Data
US 2018/0177708 A1   Jun. 28, 2018

(51) Int. Cl.
| | |
|---|---|
| A61K 8/73 | (2006.01) |
| A61K 8/46 | (2006.01) |
| A61K 8/34 | (2006.01) |
| A61K 8/97 | (2017.01) |
| A61K 8/02 | (2006.01) |
| A61Q 5/02 | (2006.01) |
| A61Q 5/12 | (2006.01) |
| A61K 8/37 | (2006.01) |
| A61K 8/44 | (2006.01) |
| A61K 8/04 | (2006.01) |

(52) U.S. Cl.
CPC ............ *A61K 8/737* (2013.01); *A61K 8/0216* (2013.01); *A61K 8/042* (2013.01); *A61K 8/345* (2013.01); *A61K 8/375* (2013.01); *A61K 8/44* (2013.01); *A61K 8/466* (2013.01); *A61K 8/73* (2013.01); *A61K 8/97* (2013.01); *A61Q 5/02* (2013.01); *A61Q 5/12* (2013.01); *A61K 2800/262* (2013.01); *A61K 2800/30* (2013.01); *A61K 2800/88* (2013.01)

(58) Field of Classification Search
CPC ....... A61Q 19/10; C11D 17/0017; A61K 8/73
USPC ................................ 510/130, 119; 424/70.1
See application file for complete search history.

(56) References Cited

U.S. PATENT DOCUMENTS

| | | | |
|---|---|---|---|
| 6,153,208 A * | 11/2000 | McAtee | A61K 8/0208 424/402 |
| 6,623,727 B2 | 9/2003 | Birkel et al. | |
| 6,673,371 B2 | 1/2004 | Brown et al. | |
| 6,719,967 B1 | 4/2004 | Brown et al. | |
| 2006/0040036 A1 | 2/2006 | Vasanthan | |
| 2012/0183484 A1 | 7/2012 | Beaumer | |
| 2013/0183361 A1 * | 7/2013 | Tamareselvy | A61K 8/8152 424/401 |
| 2016/0022557 A1 * | 1/2016 | Galleguillos | C11D 3/226 510/123 |

FOREIGN PATENT DOCUMENTS

WO    04045576 A1    6/2004

* cited by examiner

*Primary Examiner* — Gregory E Webb
(74) *Attorney, Agent, or Firm* — Maria Luisa Balasta

(57) ABSTRACT

Disclosed are compositions for treating and cleansing keratinous substrates, comprising: a polysaccharide; a cationic polymer in an amount of at least 0.1% by weight based on the total weight of the composition; an anionic surfactant chosen from sulfonate surfactants, carboxylic (carboxylate) surfactants, and mixtures thereof; a polyol; and a cosmetically acceptable carrier. The compositions can additionally contain a glyceryl ester. Also, the compositions have a gel or semi-solid structure and texture. Disclosed are methods of treating and cleansing keratinous substrates using the compositions of the invention.

24 Claims, 1 Drawing Sheet

LEFT: market product    RIGHT: Formulation #1 (inventive)

Photographic Image of a Mannequin Head Showing the Amount and Quality of the Foam Produced on the Hair Treated with Two Different Compositions

LEFT: market product    RIGHT: Formulation #1 (inventive)
Photographic Image of a Mannequin Head Showing the Amount and Quality of the Foam Produced on the Hair Treated with Two Different Compositions

.# COSMETIC COMPOSITIONS FOR TREATING KERATINOUS SUBSTRATES

FIELD OF THE INVENTION

The present application relates to cosmetic compositions for use on keratinous substrates, such as hair. In particular, it relates to compositions and methods for treating and cleansing hair.

BACKGROUND

Surfactants are widely used in aqueous based personal care, household, and industrial products. They are typically used as wetting agents, detergents, and emulsifiers. In personal care cleansing products (e.g., shampoos, body washes, facial cleansers, liquid hand soaps, etc.) the surfactant is often the most important component because it provides many of the cleansing attributes of the composition.

Although in principle any surfactant class (e.g., cationic, anionic, nonionic, amphoteric) is suitable in cleansing or cleaning applications, in practice most personal care cleansers and household cleaning products are formulated with anionic surfactants or with a combination of an anionic surfactant as the primary detersive agent with one or more secondary surfactants selected from the other surfactant classes. Anionic surfactants are often used as detersive agents in cleansers and cleaning products because of their excellent cleaning and foaming properties. From the consumer's perspective, the amount and stability of the foam directly relates to the perceived cleaning efficiency of the composition. Generally speaking, the larger the volume of foam produced and the more stable the foam, the more efficient is the perceived cleaning action of the composition. This presents a potential problem in low-surfactant formulations, as foam volume tends to decrease with decreasing surfactant concentration.

Sulfate-based surfactants (such as, for example, sodium lauryl sulfate and sodium lauryl ether sulfate) are particularly popular because of their effectiveness in cleansing, foam production, and stability. Personal care cleansers containing sulfate-based surfactants are also generally easy to thicken with typical thickeners, such as salt and cellulose-based materials. Nonetheless, these particular surfactants can be harsh and irritating to skin. For instance, over-use of sulfate-based surfactants can cause needless drying to the face and scalp, and contribute to color fading and drying of hair. Eliminating sulfate-based surfactants from cleansing compositions has been challenging because sulfate-free compositions typically have poor foaming properties, are difficult to thicken, and may not provide the desired degree of clarity or transparency. Also, the cleansing ability of sulfate-free compositions are often sub-optimal.

Thus, manufacturers of personal care and cosmetic products continue to seek formulate cleansing compositions such as hair shampoos that utilize ingredients or combinations of ingredients that can provide good cleansing benefits while at the same time, provide other attributes such as good foaming, conditioning, smoothing, and detangling properties as well as unique product textures and visual appearance that are appealing to the consumers.

BRIEF SUMMARY

The present disclosure relates to cleansing compositions. More particularly, the embodiments of the disclosure relate to compositions that are translucent in appearance and have a unique, semi solid-like gel or gel-like texture and appearance as well as a viscoelastic property. In addition, the compositions of the present disclosure relate to rinse-off compositions that when used on hair, provide conditioning, softness and detangling properties to hair. The visual appearance of translucency is typically associated with the sensation of a product being light weight on keratinous substrates such as hair or skin (i.e., does not feel heavy or does not weigh the hair down), as well as with a clean feel on said substrates.

The compositions exhibit unique viscoelastic properties and are particularly useful as cleansing compositions such as shampoos, body washes or shaving compositions.

Embodiments of the disclosure relate to a composition for treating keratinous substrates, the composition comprising:
(a) at least one polysaccharide;
(b) at least one cationic polymer present in an amount of at least 0.1% by weight based on the total weight of the composition;
(c) at least one anionic surfactant chosen from sulfonate surfactants, carboxylic (carboxylate) surfactants, and mixtures thereof;
(d) at least one polyol; and
(e) a cosmetically acceptable carrier.

The compositions of the instant disclosure exhibit effective/desirable cleansing and foaming properties. Furthermore, the compositions provide a "clean" and refreshing feel and impart conditioning or moisturizing properties to the hair. The compositions are translucent in appearance and have a jello-like or gel-like texture as well as a viscoelastic property.

It is to be understood that both the foregoing general description and the following detailed description are exemplary and explanatory only, and are not restrictive of the disclosure.

BRIEF DESCRIPTION OF THE DRAWINGS

FIG. 1 is a photographic image of a mannequin head showing the amount of foam produced from the application of a commercial product and of a formula representing the inventive composition of the present disclosure on the hair of the mannequin head in a half-head study.

It should be understood that the various aspects are not limited to the arrangements and instrumentality shown in the drawings.

DETAILED DESCRIPTION

As used herein, the expression "at least one" means one or more and thus includes individual components as well as mixtures/combinations.

In the present patent application, a species is termed as being "cationic" when it bears at least one permanent positive charge or when it can be ionized as a positively charged species, under the conditions of use of the compositions of embodiments of the disclosure (for example the medium or the pH) and not comprising any anionic filler.

A species is termed as being "nonionic" when it is neither cationic nor anionic within the meaning of the disclosure, in particular when it comprises no cationic or anionic groups within the meaning of the disclosure.

A species is termed as being "anionic" when it bears at least one permanent negative charge or when it can be ionized as a negatively charged species, under the conditions of use of the compositions of embodiments of the disclosure (for example the medium or the pH) and not comprising any cationic filler.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9% 11% and "about 2%" means 1.8% -2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" and not in the exclusive sense of "consisting only of".

"Keratinous substrates" as used herein, includes, but is not limited to keratin fibers such as hair on the human head and hair comprising eyelashes. "Keratinous substrates" as used herein, may also refer to the skin such as lips, finger nails or toe nails, and the scalp.

As used herein, the terms "applying a composition onto "keratinous substrates" as used herein, includes, and "applying a composition onto "keratinous substrates" or "keratin fibers" such as hair on a human head with at least one of the compositions of the disclosure, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present disclosure onto keratinous substrates such as hair. The term 'treat" (and its grammatical variations) as used herein also refers to contacting the surface of keratinous substrates such as hair with the compositions of the present disclosure onto "Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

The term "polymer" is understood to mean, within the meaning of the disclosure, a compound characterized by the multiple repetition of one or more species of atoms or groups of atoms, known as monomers, linked to each other in amounts sufficient to provide a set of properties that do not vary markedly with the addition or removal of one or a few of the monomers.

The term "film-forming polymer" is understood to mean a polymer which is capable of forming, by itself alone or in the presence of an additional film-forming agent, a macroscopically continuous or semi-continuous film on a support, in particular on keratinous substances, such as a cohesive film.

The term "rinse-off" is used herein to mean that a keratinous substrate such as hair is rinsed and/or washed with water either after or during the application of a composition onto the keratinous substrate, and before drying and/or styling said keratinous substrate. At least a portion of the composition is removed from the keratinous substrate during the rinsing and/or washing. A "rinse-off" product refers to a composition such as a hair care composition that is rinsed and/or washed with water either after or during the application of the composition onto the keratinous substrate, and before drying and/or styling said keratinous substrate.

The term "translucent" as used herein means that a material (phase or container) is sufficiently clear such that a pattern of one or more opaque phases may be observable.

The term "gel" or "gel-like" or "jello-like" and variations of these terms as used herein in association with the visual/physical appearance and texture of the compositions of the present disclosure means that said compositions have a self-sustaining structure which does not require physical or external support (i.e., can hold a shape) for a given period of time at constant temperature, for example, from the time of preparation to the time of application or end use. These terms can also mean that the visual/physical appearance and texture of the compositions of the present disclosure is "gelatin-like" and/or corresponds to a semi-solid. These terms can also mean that the composition is not easily pourable. The gel or jello-like structure of the compositions of the invention is hard or rigid enough such that a sufficient amount of pressure or force applied on the structure is required in order to break the structure. For example, a shearing force or a pressing action with the hands or fingers can be used in order to distribute the formula in the hand or onto a surface, such as the surface of hair.

Viscoelasticity is the property of materials that exhibit both viscous and elastic characteristics when undergoing deformation. Viscous materials resist shear flow and strain linearly with time when a stress is applied. Elastic materials strain when stretched and quickly return to their original state once the stress is removed. Viscoelastic materials have elements of both of these properties and, as such, exhibit time-dependent strain. Thus, the term "viscoelastic" as used herein with respect to the compositions of the present disclosure means that the compositions can change shape when a certain amount of pressure or force is applied to the compositions but can return to the original shape when the pressure or force is removed. Said amount of pressure or force is such that it is not sufficient to break the gel or jello-like structure of the compositions of the invention.

The compositions and methods of the present disclosure can comprise, consist of, or consist essentially of the essential elements and limitations of the disclosure described herein, as well as any additional or optional ingredients, components, or limitations described herein or otherwise useful.

An embodiment of the present disclosure is directed to a composition for treating keratinous substrates, the composition comprising:
(a) at least one polysaccharide;
(b) at least one cationic polymer present in an amount of at least 0.1% by weight based on the total weight of the composition;

(c) at least one anionic surfactant chosen from sulfonate surfactants, carboxylic (carboxylate) surfactants, and mixtures thereof;

(d) at least one polyol; and (e) a cosmetically acceptable carrier.

In an embodiment, the at least one polysaccharide is chosen from anionic polysaccharides, nonionic polysaccharides, and mixtures thereof.

In an embodiment, the at least one polysaccharide is chosen from galactans, galactomannans, galactoglucomannans, glucomannans, glucopyranoses, polyuronic acids, and mixtures thereof.

In an embodiment, the at least one polysaccharide includes galactans chosen from carrageenans, agar, and mixtures thereof.

In an embodiment, the at least one carrageenan is chosen from lamda carrageenan, kappa carrageenan, iota carrageenan, and mixtures thereof.

In an embodiment, the at least one polysaccharide ranges from about 0.5% to about 10% by weight, or from about 1% to about 8% by weight, or from about 1.5% to about 5% by weight, based on the total weight of the composition, including all ranges and subranges therebetween.

In an embodiment, the at least one cationic polymer is chosen from cationic cellulose derivatives, cationic gum derivatives, polymer derivatives of diallyldimethyl ammonium chloride, polymer derivatives of methacrylamidopropyltrimethylammonium chloride, and mixtures thereof.

The composition according to claim 8, wherein the at least one cationic polymer is chosen from polyquaternium-7, polyquaternium-10, guar hydroxypropyltrimonium chloride, and mixtures thereof.

The composition according to claim 9, wherein the at least one cationic polymer is guar hydroxypropyltrimonium chloride (also known as hydroxypropyl guar hydroxypropyltrimonium chloride).

In an embodiment, the amount of the at least one cationic polymer ranges from about 0.1% to about 10% by weight, based on the total weight of the composition, including all ranges and subranges therebetween.

In an embodiment, the at least one anionic surfactant is chosen from sulfonate surfactants, carboxylic (carboxylate) surfactants, and mixtures thereof, and preferably chosen from sulfonate surfactants such as sodium lauroyl sarcosinate, sodium lauryl sulfoacetate, sodium isethionate, sodium cocoyl isethionate, disodium laureth sulfosuccinate, sodium lauroyl methyl isethionate, and mixtures thereof.

In an embodiment, the at least one anionic surfactant is chosen from carboxylic (carboxylate) surfactants such as sodium cocoyl glutamate, disodium cocoyl glutamate, and mixtures thereof.

In an embodiment, the composition of the present disclosure is essentially free of sulfate surfactants.

In an embodiment, the amount of the at least one anionic surfactant ranges from about 0.5% to about 15% by weight, based on the total weight of the composition, including all ranges and subranges therebetween.

In an embodiment, the at least one polyol is a compound containing at least two hydroxyl groups and containing from 2 to 8 carbon atoms, and wherein the at least one polyol is preferably chosen from ethylene glycol, propylene glycol, 1,3-butylene glycol, pentylene glycol, hexylene glycol, dipropylene glycol, glycerin, and mixtures thereof.

In an embodiment, the amount of the least one polyol ranges from about 0.1% to about 10% by weight, including all ranges and subranges therebetween.

In an embodiment, the at least one cosmetically acceptable carrier comprises water or a mixture of water and an organic solvent other than the at least one polyol of the present invention.

In an embodiment, the composition further comprises a plant-based or fruit-based material.

In an embodiment, the composition further comprises a plant-based or fruit-based material that is included in the composition as an aqueous solution containing the plant-based or fruit-based material.

In an embodiment, the aqueous solution containing the plant-based or fruit-based material is present in the composition of the present disclosure in an amount of at least 10% by weight, or ranging from about 10% to about 70% by weight, including all ranges and subranges therebetween.

In an embodiment, the composition further comprises at least one glyceryl ester chosen from glyceryl monoesters of C16-C22 saturated, unsaturated and branched chain fatty acids, and mixtures thereof.

In an embodiment, the least one glyceryl ester is chosen from glyceryl oleate, glyceryl monostearate (or glyceryl stearate), glyceryl distearate, glyceryl monoisostearate, glyceryl monopalmitate, glyceryl monobehenate, and mixtures thereof.

In an embodiment, the amount of the least one glyceryl ester ranges from about 0.05% to about 5% by weight, based on the total weight of the composition, including all ranges and subranges therebetween.

In an embodiment, the composition is translucent.

In an embodiment, the composition is a viscoelastic gel.

In an embodiment, the composition has a gel-like or semi-solid like or jello-like appearance, structure, and texture.

In an embodiment, the keratinous substrates include hair.

In an embodiment, the composition is a shampoo or a cleansing or a conditioning shampoo composition.

An embodiment of the present disclosure is directed to a method for treating and/or cleansing a keratinous substrate, the method comprising contacting the keratinous substrate with a composition comprising the above-described compositions of the present disclosure.

In an embodiment, the method further comprises leaving the composition on the keratinous substrate for a period of time and then rinsing the keratinous substrate with water.

In another embodiment, the invention of the present disclosure is directed to a translucent composition for cleansing hair, the composition comprising:

(a) from about 1% to about 8% by weight of at least one polysaccharide chosen from galactans, glucopyranoses, gellan gums, scleroglucan gums, and mixtures thereof;

(b) from about 0.4% to about 4% by weight of at least one cationic polymer chosen from cationic gum derivatives;

(c) from about 1% to about 12% by weight of at least one anionic surfactant chosen from sulfonate surfactants, carboxylic (carboxylate) surfactants, and mixtures thereof;

(d) from about 0.1% to about 8% by weight at least one polyol compound containing at least two hydroxyl groups and containing from 2 to 8 carbon atoms, and wherein the at least one polyol is preferably chosen from ethylene glycol, propylene glycol, 1,3-butylene glycol, pentylene glycol, hexylene glycol, dipropylene glycol, glycerin, and mixtures thereof;

(e) a cosmetically acceptable carrier; and (f) from about 0.075% to about 4% by weight of at least one glyceryl ester chosen from glyceryl monoesters of C16-C22 saturated, unsaturated and branched chain fatty acids, and mixtures thereof;

all weights being based on the total weight of the composition.

In another embodiment, the invention of the present disclosure is directed to a translucent composition for cleansing hair, the composition comprising:
(a) from about 1.5% to about 5% by weight of at least one polysaccharide chosen from carrageenans, preferably iota carrageenan, gellan gums, *sclerotium* gums, and mixtures thereof;
(b) from about 0.4% to about 2% by weight of at least one cationic polymer chosen from guar hydroxypropyltrimonium chloride;
(c) from about 1.2% to about 10% by weight of at least one anionic surfactant chosen from sodium lauroyl sarcosinate, sodium lauryl sulfoacetate, sodium isethionate, sodium cocoyl isethionate, disodium laureth sulfosuccinate, sodium lauroyl methyl isethionate, sodium cocoyl glutamate, disodium cocoyl glutamate, and mixtures thereof;
(d) from about 0.1% to about 6% by weight at least one polyol compound chosen from ethylene glycol, propylene glycol, 1,3-butylene glycol, pentylene glycol, hexylene glycol, dipropylene glycol, glycerin, and mixtures thereof;
(e) a cosmetically acceptable carrier; and
(f) optionally, from about 0.1% to about 3% by weight of at least one glyceryl ester chosen from glyceryl oleate, glyceryl monostearate (or glyceryl stearate), glyceryl distearate, glyceryl monoisostearate, glyceryl monopalmitate, glyceryl monobehenate, and mixtures thereof;

all weights being based on the total weight of the composition.

In another embodiment, the invention of the present disclosure is directed to a translucent composition for cleansing hair, the composition comprising:
(a) from about 1% to about 8% by weight of at least one polysaccharide chosen from galactans, glucopyranoses, gellan gums, *sclerotium* gums, and mixtures thereof;
(b) from about 0.4% to about 4% by weight of at least one cationic polymer chosen from cationic gum derivatives;
(c) from about 1% to about 12% by weight of at least one anionic surfactant chosen from sulfonate surfactants, carboxylic (carboxylate) surfactants, and mixtures thereof;
(d) from about 0.1% to about 8% by weight at least one polyol compound containing at least two hydroxyl groups and containing from 2 to 8 carbon atoms, and wherein the at least one polyol is preferably chosen from ethylene glycol, propylene glycol, 1,3-butylene glycol, pentylene glycol, hexylene glycol, dipropylene glycol, glycerin, and mixtures thereof;
(e) a cosmetically acceptable carrier;
(f) optionally, from about 0.075% to about 4% by weight of at least one glyceryl ester chosen from glyceryl monoesters of C16-C22 saturated, unsaturated and branched chain fatty acids, and mixtures thereof; and
(g) optionally, at least 10% by weight of *aloe (barbadensis)* leaf juice;

all weights being based on the total weight of the composition.

Any one of the above-described compositions of the present disclosure may include include one or more nonionic surfactants. Non-limiting examples of useful nonionic surfactants include fatty alcohols, alkoxylated fatty alcohols, alkylphosphates, alkylpolyglucosides, fatty acid alkanolamides, and mixtures thereof.

Any one of the above-described compositions of the present disclosure may include include one or more amphoteric surfactants. Non-limiting examples of amphoteric surfactants include betaines, sultaines, amphoacetates, amphoproprionates, and mixtures thereof.

Any one of the above-described compositions of the present disclosure may include include one or more non-polymeric cationic conditioning agents, for example, quaternary ammonium compounds such as behentrimonium chloride, cetrimonium chloride, behentromonium methosulfate, and mixture thereof.

It has been surprisingly and unexpectedly discovered that the compositions according to the disclosure are stable over time at room temperature, exhibit no visible phase separation, are translucent in appearance, and impart cosmetic effects to keratinous substrates even after the compositions are rinsed off with water. When used on hair, the hair easy to detangle and comb through, feels conditioned, smoother, and softer, and is more manageable and has more discipline (lees fly-aways and/or less frizzy). It is possible that these effects remain on the hair even after several washings of the hair.

It was also surprisingly and unexpectedly discovered that the compositions according to the disclosure produced good and desirable foam quality with respect to abundance of foam and stability of the foam when the compositions were applied onto a wet substrate such as hair or skin during a cleansing or shampoo process. The foam quality was surprisingly and unexpectedly found to be better than a comparative commercial product which is described in the example section.

In addition, it was surprisingly and unexpectedly discovered that the compositions according to the disclosure exhibited a unique viscoelastic texture. Due to their viscoelastic properties, the compositions of the instant disclosure exhibit a unique behavior that consumers find especially distinctive.

As mentioned above, the compositions are mild/gentle and provide conditioning and hydrating properties. Therefore, the compositions may also be used in methods for conditioning or hydrating the hair. Thus, it was surprisingly discovered that the compositions of the present disclosure imparted a very good balance of cleansing, foaming, and conditioning benefits to keratinous substrates, while providing a texture and visual appearance that is aesthetically pleasing and desirable. At the same time, it was found that the gel-like compositions of the present invention have a good distribution quality (spreadability) on keratinous substrates, a quality that consumers desire with gel types of products.

Polysaccharide

Some polysaccharide can also be called polysaccharide hydrocolloids which can act as gellants (or gelling agents). Gelling agents are a subset of thickeners and are known to those skilled in the art. Gellants are polymers that can form a gel on setting or upon acidification or treatment with a divalent or monovalent cation. A gel may be defined in general as a solid, jelly like material that can have properties ranging from soft and weak to hard and tough. Gellants are known to provide structure to compositions through chain interactions or entanglements enabling the formation of gels, either alone or upon addition of a monovalent or divalent cation or by addition of a proton source. Y. Nitta et al., Gelation and gel properties of polysaccharides gellan gum and tamarind xyioglucan, J. Biol. Macromol. 5(3):47-52 (2005).

In the context of the current invention, the polysaccharides are preferably gellants. Non-limiting examples of such gelling polysaccharide hydrocolloids are selected from polymers comprising polysaccharides, and derivatives thereof that contain one or more of the following monosaccharide units: galactose, mannose, glucoside, glucose, xylose, arabinose, fructose, glucuronic acid, or pyranosyl sulfate. These polysaccharides include, but are not limited to cellulose derivatives, homopolysaccharides, heteropolysaccharides, anionic polysaccharides and neutral or nonionic polysaccharides.

Mention may in particular be made, as polysaccharides according to the invention, of anionic or non-ionic microbial gums.

Within the meaning of the present invention, "microbial gums" is understood to mean substances synthesized by fermentation of sugars by microorganisms.

Mention may in particular be made of scleroglucan gums such as *sclerotium* gums produced by *Sclerotium rolfsii* and the gellan gums produced by *Pseudomonas elodea* or *Sphingomonias*.

Non-limiting examples of cellulose derivatives include hydroxyethylcellulose, carboxymethyl cellulose, carboxymethyl hydroxyethyl cellulose, and mixtures thereof. In a particular embodiment, the cellulose derivative is hydroxyethylcellulose.

Mention may also be made, as polysaccharides according to the invention, of those chosen from glucans, modified or unmodified starches (such as those resulting, for example, from cereals, such as wheat, maize or rice, from vegetables, such as yellow pea, or from tubers, such as potato or cassava), amylose, amylopectin, glycogen, dextrans, celluloses and their derivatives (methylcelluloses, hydroxyalkylcelluloses, ethylhydroxyethylcelluloses, carboxymethylcelluloses), mannans, xylans, lignins, arabans, galactans, galacturonans, chitin, chitosans, glucuronoxylans, arabinoxylans, xyloglucans, glucomannans, pectic acids and pectins, arabinogalactans, carrageenans, agars, gums arabic, gums tragacanth, ghatti gums, karaya gums, locust bean gums, galactomannans, such as guar gums and their non-ionic derivatives (hydroxypropyl guar), and their mixtures.

In an embodiment the polysaccharide is selected from a homopolysaccharide, most preferably *sclerotium* gum.

In an embodiment the polysaccharide is selected from a heteropolysaccharide, most preferably gellan gum.

In another preferred embodiment the polysaccharide is selected from an anionic polysaccharide. Suitable anionic polysaccharides include carrageenans, gellan gums, scleroglucan gums, and mixtures thereof. In another preferred embodiment the polysaccharide is selected from a neutral polysaccharide selected from gums such as galactomannan gum and glucomannan gum, agarose, and mixtures thereof.

Mention may be made, as anionic starches, of carboxymethyl starch or starch phosphate.

In an embodiment the polysaccharide is a galactomannan gum, preferably *ceratonia siliqua* gum.

In an embodiment, the at least one polysaccharide in the compositions of the present disclosure is not a cationic polysaccharide or is not cationically charged.

The at least one polysaccharide in the compositions of the present disclosure may preferably be chosen from galactans, galactomannans, galactoglucomannans, glucomannans, glucopyranoses, polyuronic acids, gellan gums, scleroglucan gums such as *sclerotium* gums, and mixtures thereof.

In an embodiment, the at least one polysaccharide is chosen such that the resulting composition of the invention achieves a gel or jello-like structure that is not pourable and has a self-sustaining structure for a given period of time at constant temperature, and has viscoelastic properties.

In an embodiment, the at least one polysaccharide is chosen from carrageenans, gellan gums, and mixtures thereof.

In an embodiment, the at least one polysaccharide includes at least one carrageenan chosen from lambda carrageenan, kappa carrageenan, iota carrageenan, and mixtures thereof.

In an embodiment, the at least one polysaccharide is a carrageenan chosen from iota carrageenan.

In an embodiment, the at least one polysaccharide is a carrageenan comprising lambda carrageenan and iota carrageenan.

In an embodiment, the at least one polysaccharide is a carrageenan comprising kappa carrageenan and iota carrageenan.

The at least one polysaccharide is present in the compositions of the present disclosure in an amount ranging from about 0.5% to about 10% by weight, or from about 1% to about 8% by weight, or from about 1.5% to about 5% by weight, based on the total weight of the composition, including all ranges and subranges there between.

In various embodiments, the at least one polysaccharide is present in the compositions of the present disclosure in an amount of about 0.5%, 0.6%, 0.7%, 0.8%, 0.9%, 1%, 1.1%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.2%, 4.4%, 4.5%, 4.6%, 4.8%, 5%, 5.2%, 5.4%, 5.5%, 5.6%, 5.8%, 6%, 6.2%, 6.4%, 6.5%, 6.6%, 6.8%, 7%, 7.2%, 7.4%, 7.5%, 7.6%, 7.8%, 8%, 8.5%, 9%, 9.5%, or 10%, by weight, based on the total weight of the composition.

Cationic Polymer

The composition according to the invention comprises at least one cationic polymer. The cationic polymer used in the invention comprises homopolymers, copolymers, and mixtures thereof.

Non-limiting examples of cationic polymers useful in the invention include, for example, cationic cellulose derivatives, such as for example polyquaternium-10; cationic gum derivatives such as for example gum derivatives, including particularly guar hydroxypropyltrimonium chloride; polymer derivatives of diallyldimethyl ammonium chloride ("poly-DADMAs") and of methacrylamidopropyltrimethylammonium chloride ("poly-MAPTACs"), and mixtures thereof Non-limiting examples of poly-DADMAs and poly-polyMAPTACs include, polyquaternium-4, polyquaternium-5, polyquaternium-6, polyquaternium-7, polyquaternium-22, polyquaternium-37, polyquaternium-39, polyquaternium-47, polyquaternium-53, and mixtures thereof.

The composition according to the invention preferably comprises cationic polymers known under the INCI names polyquaternium-7, polyquaternium-10, guar hydroxypropyltrimonium chloride (hydroxypropyl guar hydroxypropyltrimonium chloride), and mixtures thereof.

In an embodiment, the cationic polymer of the present invention is chosen from guar hydroxypropyltrimonium chloride (hydroxypropyl guar hydroxypropyltrimonium chloride).

The cationic polymer is present in an amount ranging from about 0.1% to about 10% by weight, or from about 0.2% to about 5% by weight or from about 0.4% to about 2% by weight, based on the total weight of the composition, including all ranges and subranges therebetween.

In some embodiments, the cationic polymer is present in an amount of about 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.1%, 2.2%, 2.3%, 2.4%, 2.5%, 2.6%, 2.7%, 2.8%, 2.9%, 3%, 3.5%, 4%, 4.5%, 5%, 6%, 7%, 8%, 9% and 10% by weight, based on the total weight of the composition Anionic Surfactants The at least one anionic surfactant of the present invention may be chosen from sulfonate surfactants, carboxylic (or carboxylate) surfactants, and mixtures thereof.

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

It is understood in the present description that:

carboxylate anionic surfactants comprise at least one carboxylic or carboxylate function (—COOH or —COO—) and may optionally also comprise one or more sulfate and/or sulfonate functions; and the sulfonate anionic surfactants comprise at least one sulfonate function (—SO3H or —SO3) and may optionally also comprise one or more carboxylate functions.

The carboxylic anionic surfactants that may be used thus comprise at least one carboxylic or carboxylate function (—COOH or —COO—).

They may be chosen from the following compounds:

acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds;

the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, especially polyoxyethylenated, and preferably comprising from 1 to 50 ethylene oxide units and better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo.

The polyoxyalkylenated alkyl (amido) ether carboxylic acids that may be used are preferably chosen from those of formula (1):

$$R_1-(OC_2H_4)_n-OCH_2OOOA \quad (1)$$

in which:

R1 represents a linear or branched C6-C24 alkyl or alkenyl radical, an alkyl(C8-C9)phenyl radical, a radical R2CONH—CH2-CH2- with R2 denoting a linear or branched C9-C21 alkyl or alkenyl radical, preferably, R1 is a C8-C20 and preferably C8-C18 alkyl radical, and aryl preferably denotes phenyl, n is an integer or decimal number (average value) ranging from 2 to 24 and preferably from 2 to 10, A denotes H, ammonium, Na, K, Li, Mg or a monoethanolamine or triethanola-mine residue.

It is also possible to use mixtures of compounds of formula (1), in particular mixtures of compounds containing different groups R1.

The polyoxyalkylenatedalkyl(amido) ether carboxylic acids that are particularly preferred are those of formula (1) in which:

R1 denotes a C12-C14 alkyl, cocoyl, oleyl, nonylphenyl or octylphenyl radical,

A denotes a hydrogen or sodium atom, and n varies from 2 to 20 and preferably from 2 to 10.

Even more preferentially, use is made of compounds of formula (1) in which R denotes a C12 alkyl radical, A denotes a hydrogen or sodium atom and n ranges from 2 to 10.

The carboxylic anionic surfactants may be chosen, alone or as a mixture, from:

acylglutamates, especially of C6-050 or of C6-C30 or of C6-C24 or even C12-C20, such as stearoylglutamates, cocoyl glutamates, and in particular disodium stearoylglutamate or disodium cocoyl glutamate or sodium cocoyl glutamate;

acylsarcosinates, especially of C6-050 or of C6-C30 or of C6-C24 or even C12-C20, such as palmitoylsar-cosinates, and in particular sodium palmitoylsarcosinate;

acyllactylates, especially of C6-050 or of C6-C30 or of C6-C24 or C12-C20, such as behenoyllac-tylates, and in particular sodium behenoyllactylate;

C6-050 or C6-C30 or C6-C24 and especially C12-C20 acylglycinates;

(C6-C30)alkyl ether carboxylates and especially (C12-C20)alkyl ether carboxylates;

polyoxyalkylenated (C6-C30)alkyl(amido) ether carboxylic acids, in particular those comprising from 2 to 50 ethylene oxide groups;

in particular in the form of alkali metal or alkaline-earth metal, ammonium or amino alcohol salts.

The sulfonate anionic surfactants that may be used comprise at least one sulfonate function (—SO3H or —SO3-).

They may be chosen from the following compounds:

alkylsulfonates, alkyla-midesulfonates, alkylarylsulfonates, α-olefinsulfonates, paraffin sulfonates, alkyl-sulfosuccinates, alkyl ether sulfosuccinates, alkylamidesulfosuccinates, alkyl-sulfoacetates, N-acyltau rates, acylisethionates; alkylsulfolaurates; and also the salts of these compounds;

the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, especially polyoxyethylenated, and then preferably comprising from 1 to 50 ethylene oxide units and better still from 2 to 10 ethylene oxide units.

The sulfonate anionic surfactants may be chosen, alone or as a mixture, from:
- C6-O50 or C6-C30 or C6-C24 and especially C12-C20 alkylsulfosuccinates, especially laurylsulfosuccinates;
- C6-O50 or C6-C30 or C6-C24 and especially C12-C20 alkyl ether sulfosuccinates;
- (C6-C30)acylisethionates and preferably (C12-C18) acylisethionates, in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:
- C6-C24 and especially C12-C20 alkylsulfosuccinates, especially laurylsulfosuccinates;
- C6-C24 and especially C12-C20 alkyl ether sulfosuccinates;
- (C6-C24)acylisethionates and preferably (C12-C18) acylisethionates;
- C6-C24 and especially C12-C20 acylsarcosinates; especially palmitoylsar-cosinates;
- (C6-C24)alkyl ether carboxylates, preferably (C12-C20) alkyl ether carboxylates;
- polyoxyalkylenated (C6-C24)alkyl(amido) ether carboxylic acids and salts there-of, in particular those comprising from 2 to 50 alkylene oxide and in particular ethylene oxide groups;
- C6-C24 and especially C12-C20 acylglutamates;
- C6-C24 and especially C12-C20 acylglycinates;

in particular in the form of alkali metal or alkaline-earth metal, ammonium or amino alcohol salts.

In some embodiments, the at least one anionic surfactant of the present invention is chosen from sulfonate surfactants.

In certain embodiments, the at least one anionic surfactant of the present invention is preferably chosen from sodium lauroyl sarcosinate, sodium lauryl sulfoacetate, sodium isethionate, sodium cocoyl isethionate, disodium laureth sulfosuccinate, sodium lauroyl methyl isethionate, and mixtures thereof.

In some embodiments, the at least one anionic surfactant of the present invention is chosen from carboxylic (carboxylate) surfactants such as sodium cocoyl glutamate, disodium cocoyl glutamate, and mixtures thereof.

In one embodiment of the present invention, the at least one anionic surfactant is selected from sodium lauroyl sarcosinate.

In one embodiment of the present invention, the at least one anionic surfactant comprises sulfonate surfactants, and carboxylic (carboxylate) surfactants.

The at least one anionic surfactant chosen from sulfonate surfactants and/or carboxylic (carboxylate) surfactants is present in the compositions of the invention in a total amount of from about 0.5% to about 15% by weight, or from about 1% to about 12% by weight, or from about 1.2% to about 10% by weight, based on the total weight of the composition, including all ranges and subranges therebetween.

In a particular embodiment, the total amount of anionic surfactants chosen from sulfonate surfactants and/or carboxylic (carboxylate) surfactants is at about 0.5%, 0.6%, 0.7%, 0.8%, 0.9%, 1%, 1.1%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.2%, 4.4%, 4.5%, 4.6%, 4.8%, 5%, 5.2%, 5.4%, 5.5%, 5.6%, 5.8%, 6%, 6.2%, 6.4%, 6.5%, 6.6%, 6.8%, 7%, 7.2%, 7.4%, 7.5%, 7.6%, 7.8%, 8%, 8.5%, 9%, 9.5%, 10%, 10.5%, 11%, 11.5%, 12%, 12.5%, 13%, 13.5%, 14%, 14.5%, or 15% by weight, based on the total weight of the composition.

The compositions of the present invention may further comprise sulfate-based anionic surfactants comprising at least one sulfate function (—OSO3H or —OSO3-).

They may be chosen from the following compounds:
alkyl sulfates, alkyl ether sulfates, alkylamido ether sulfates, alkylaryl polyether sulfates, monoglyceride sulfates; and also the salts of these compounds;
the alkyl groups of these compounds comprising from 6 to 30 carbon atoms, especially from 12 to 28, better still from 14 to 24 or even from 16 to 22 carbon atoms;
the aryl group preferably denoting a phenyl or benzyl group;
these compounds possibly being polyoxyalkylenated, especially polyoxyethylenated, and then preferably comprising from 1 to 50 ethylene oxide units and better still from 2 to 10 ethylene oxide units.

The sulfate anionic surfactants can be chosen, alone or as a mixture, from:
alkyl sulfates, especially of C6-C24 or even C12-C20,
alkyl ether sulfates, especially of C6-C24 or even C12-C20, preferably comprising from 2 to 20 ethylene oxide units;

in particular in the form of alkali metal or alkaline-earth metal, ammonium or amino alcohol salts. Examples of sulfate-based anionic surfactants are sodium lauryl sulfate and sodium laureth sulfate.

In one embodiment of the present invention, the composition is substantially free of anionic surfactants selected from sulfate-based surfactants.

The term "substantially free" as used herein means that there is less than 1% by weight, of sulfate-based anionic surfactants added to the composition, and the term does not refer to or does not include sulfate-based anionic surfactants that may be present in raw materials as commercially available from suppliers.

Polyol

The at least one polyol of the present invention is a compound containing at least two hydroxyl groups and containing from 2 to 8 carbon atoms. The at least one polyol may be chosen from glycerin, and/or from glycols such as ethylene glycol, propylene glycol, 1,3-butylene glycol, pentylene glycol, hexylene glycol, dipropylene glycol, and/or from polyol ethers and/or from glycol ethers and mixtures thereof.

In an embodiment, the at least one polyol is preferably chosen from glycerin.

In an embodiment, the amount of the least one polyol ranges from about 0.1% to about 10% by weight, or from about 0.1% to about 8% by weight, or from about 0.1% to about 6% by weight, or from about 0.5% to about 7% by weight, or from about 1% to about 6% by weight, or from about 6% to about 10% by weight, based on the total weight of the composition, including all ranges and subranges therebetween.

In a particular embodiment, the total amount of polyols is at about 0.1%, 0.2%, 0.3%, 0.4%, 0.5%, 0.6%, 0.7%, 0.8%, 0.9%, 1%, 1.1%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.2%, 4.4%, 4.5%, 4.6%, 4.8%, 5%, 5.2%, 5.4%, 5.5%, 5.6%, 5.8%, 6%, 6.2%, 6.4%, 6.5%, 6.6%, 6.8%, 7%, 7.2%, 7.4%, 7.5%, 7.6%, 7.8%, 8%, 8.5%, 9%, 9.5%, or 10%, by weight, based on the total weight of the composition.

Cosmetically Acceptable Carrier

The cosmetically acceptable carrier of the compositions according to various embodiments of the disclosure can comprise water in amounts of about 95% or less, such as from about 95% to about 5% by weight, or about 90%, 80%, 70%, 60%, 50%, 40%, 30%, 20%, or 10%, by weight, based on the total weight of the composition, including all ranges and subranges therebetween. Additionally, water can be present in the compositions of the present disclosure in the amount of from about 20% to about 95% by weight, from about 40% to about 90% by weight, or from about 50% to about 80% by weight, based on the total weight of the compositions, including all ranges and subranges therebetween.

In an embodiment, the at least one cosmetically acceptable carrier comprises water or a mixture of water and an organic solvent other than the at least one polyol of the present invention and selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, isododecane, acetone, propylene carbonate, benzyl alcohol, and mixtures thereof.

Glyceryl Ester

The glyceryl esters of the present invention include, but are not limited to, glyceryl monoesters, such as glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof.

The glyceryl esters in the compositions of the present invention may also be referred to as nonionic co-emulsifiers.

In one embodiment, the glyceryl ester is chosen from glyceryl oleate, glyceryl monostearate (glyceryl stearate), glyceryl monoisostearate, glyceryl monopalmitate, glyceryl monobehenate, and mixtures thereof.

In one embodiment, the glyceryl ester is chosen from glyceryl oleate.

In various embodiments, the amount of the least one glyceryl ester ranges from about 0.05% to about 5% by weight, or from about 0.075% to about 4% by weight, or from about 0.1% to about 3% by weight, or from about 0.2% to about 2% by weight, or from about 0.2% to about 1% by weight, based on the total weight of the composition, including all ranges and subranges therebetween.

In some embodiments, the total amount of the at least one glyceryl ester is about 0.05%, 0.075%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.86%, 0.9%, 0.95%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, or 5%, by weight of active material, based on the total weight of the composition.

Plant-Based or Fruit-Based Materials

The composition of the present invention may further comprise a plant-based or fruit-based material such as vegetable extracts, fruit extracts, and mixtures thereof.

In an embodiment, the composition further comprises a plant-based or fruit-based material that is included in the composition as an aqueous solution containing the plant-based or fruit-based material.

A suitable example of aqueous solution containing a plant-based or fruit-based material is aloe (*barbadensis*) leaf juice.

In an embodiment, the aqueous solution containing the plant-based or fruit-based material is present in the composition of the present disclosure in an amount of at least 10% by weight, or ranging from about 10% to about 75% by weight, or from about 10% to about 55% by weight, or from about 20% to about 50% by weight, from about 30% to about 45% by weight, based on the total weight of the composition, including all ranges and subranges therebetween.

In certain embodiments, the aqueous solution containing the plant-based or fruit-based material is present in the compositions according to the disclosure in an amount of about 10%, about 15%, 20%, 25%, 30%, 35%, 40%, 45%, 50%, 55%, 60%, 65%, 70%, or 75%, based on the total weight of the composition.

In other embodiments, the plant-based or fruit-based material is present in the composition of the present disclosure in an active amount ranging from about 0.05% to about 120% by weight, or from about 0.1% to about 15% by weight, or from about 0.15% to about 10% by weight, based on the total weight of the composition, including all ranges and subranges therebetween.

In some embodiments, the plant-based or fruit-based material is present in the composition of the present disclosure in an active amount of about 0.05%, 0.075%, 0.1%, 0.125%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.86%, 0.9%, 0.95%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, or 5%, by weight, based on the total weight of the composition.

pH

The pH of the compositions according to the disclosure generally ranges from about 3 to about 7, for example from about 5 to about 6.5, or from about 5 to about 6.0, or from about 3.5 to about 5, or from about 4 to about 5, including ranges and subranges therebetween. In certain embodiments, the pH of the compositions according to the disclosure is at about 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.2, 6.4, 6.6, 6.8, and 7.

Additional Components

The composition according to the disclosure may also comprise additives chosen from nonionic and anionic polymers, rheology modifiers, thickening and/or viscosity modifying agents other than the claimed polysaccharides, associative or non-associative polymeric thickeners, non-polymeric thickeners, non-polymeric surfactants (nonionic, cationic or amphoteric), nacreous agents, dyes or pigments, fragrances, mineral, plant or synthetic oils, waxes, vitamins, proteins including ceramides, vitamins, UV-screening agents, free-radical scavengers, antidandruff agents, hairloss counteractants, hair restorers, preserving agents, pH stabilizers, organic solvents, and mixtures thereof. A person skilled in the art will take care to select the optional additives and the amount thereof such that they do not harm the properties of the compositions of the present disclosure.

If present in the composition, these additives are generally present in an amount ranging up to about 40% by weight of active material relative to the total weight of the composition, such as up to about 30%, up to about 20%, up to about 15%, up to about 10%, up to about 5%, such as from 0% to 20%.

The compositions of certain embodiments may comprise stabilizers, for example sodium chloride, magnesium dichloride or magnesium sulfate.

The rheology modifiers and thickening/viscosity-modifying agents that may be employed in compositions of the present disclosure may include any water-soluble or water-dispersible compound that is compatible with the compositions of the disclosure.

The compositions may be packaged in various forms, especially in bottles, or in jars.

Processes/Methods

The compositions according to the disclosure may be prepared according to techniques that are well known to those skilled in the art.

Embodiments of the disclosure also relate to a process for treating keratinous materials, such as hair, which consists in applying an effective amount of a composition as defined above to the said keratinous materials, and in rinsing, for example with water, after an optional leave-on time.

Certain embodiments also relate to a process for cleansing keratinous materials, such as hair, which consists in applying an effective amount of a composition to the said keratinous materials, and rinsing, for example with water, after an optional leave-on time. The term "effective amount" is used herein refers to an amount sufficient to produce visible foaming on the keratinous materials and clean said keratinous materials or provide a clean feeling to the said keratinous materials.

In some embodiments, keratinous materials, such as hair, may be washed or cleansed by a first step of applying the composition of the present invention, with an optional leave-on time, followed by a second step of applying a conditioner composition onto hair, with an optional step of rinsing the hair with water between the two first and second steps, and optionally rinsing the conditioner composition, for example with water, after an optional leave-on time.

In some embodiments, when the composition of the present invention has a gel or jello-like structure, the hands or fingers are used to apply pressure or a shearing force on a selected amount of the composition (e.g., an effective amount) in order to break its gel or jello-like structure before applying it onto keratinous materials such as hair.

The compositions may be applied to keratinous substrates, such as the hair, and subsequently rinsed off. In various embodiments, the compositions comprise hair care compositions for cleansing the hair, and in various embodiments the hair care composition will traditionally be rinsed off the hair within a short period of time after application to the hair, such as a period of time up to about 10 minutes, up to about 5 minutes, or up to about 2 minutes after application to the hair.

In various embodiments, processes according to the disclosure comprise applying the compositions described onto keratinous substrates, such as the hair, and subsequently rinsing the compositions off. The processes may, in various embodiments, impart cleansing, conditioning and/or detangling properties to the keratinous substrate to which the composition is applied, even after the composition is rinsed off. The processes may additionally impart long lasting conditioning and manageability to the keratinous substrates.

As used herein, the method/process and composition disclosed herein may be used on the hair that has not been artificially dyed, pigmented or permed.

As used herein, the method/process and composition disclosed herein may be also used on the hair that has been artificially dyed, pigmented or permed.

EXAMPLES

The following Examples are intended to be non-restrictive and explanatory only, with the scope of the disclosure being defined by the claims.

The ingredient amounts in the compositions/formulas described below are expressed in % by weight, based on the total weight of the composition/formula.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective measurements. The following examples are intended to illustrate the disclosure without limiting the scope as a result.

Example 1

TABLE 1

| | FORMULATIONS* | | | | | | | | | | | | |
|---|---|---|---|---|---|---|---|---|---|---|---|---|---|
| | Fla #1 | Fla #2 | Fla #3 | Fla #4 | Fla #5 | Fla #6 | Fla #7 | Fla #8 | Fla #9 | Fla #10 | Fla #11 | Fla #12 | Fla #13 |
| INCI US (ingredient name) | | | | | | | | | | | | | |
| CARRAGEENAN | 3 | 3 | 3 | 3 | 3 | 3 | 3 | 3 | 3 | 3 | 3 | 3 | 3 |
| SCLEROTIUM GUM | — | — | — | 0.2 | — | — | — | — | — | — | — | — | — |
| HYDROXYPROPYL GUAR HYDROXYPROPYLTRIMONIUM CHLORIDE | 0.7 | 0.7 | 0.7 | 0.3 | 0.3 | 0.7 | — | 0.7 | 0.7 | 0.7 | 0.7 | 0.7 | 0.7 |
| GLYCERYL OLEATE | 1 | — | 0.1 | — | — | — | — | — | 3 | 1 | 1 | 1 | 1 |
| DISODIUM LAURETH SULFOSUCCINATE | 2.7 | 2.7 | 2.7 | — | — | 2.7 | 2.7 | 2.7 | 2.7 | — | — | 0.9 | 5.4 |
| SODIUM LAURYL SULFOACETATE | 1.05 | 1.05 | 1.05 | — | — | 1.05 | 1.05 | 1.05 | 1.05 | — | — | 0.35 | 2.1 |

TABLE 1-continued

FORMULATIONS*

| | Fla #1 | Fla #2 | Fla #3 | Fla #4 | Fla #5 | Fla #6 | Fla #7 | Fla #8 | Fla #9 | Fla #10 | Fla #11 | Fla #12 | Fla #13 |
|---|---|---|---|---|---|---|---|---|---|---|---|---|---|
| DISODIUM COCOYL GLUTAMATE | — | — | — | 3.03 | 3.03 | — | — | — | — | — | — | — | — |
| SODIUM COCOYL GLUTAMATE | — | — | — | 0.72 | 0.72 | — | — | — | — | — | — | — | — |
| SODIUM LAURETH SULFATE | — | — | — | — | — | — | — | — | — | 2.70 | — | — | — |
| SODIUM LAURYL SULFATE | — | — | — | — | — | — | — | — | — | — | 2.70 | — | — |
| GLYCERIN | 6 | 6 | 6 | 6 | 6 | 0.1 | 6 | 20 | 6 | 6 | 6 | 6 | 6 |
| ALOE BARBADENSIS LEAF JUICE** | — | — | — | 44.9 | 44.9 | — | — | — | — | — | — | — | — |
| ADDITIVES*** | <2.0 | <2.0 | <2.0 | <2.0 | <2.0 | <2.0 | <2.0 | <2.0 | <2.0 | <2.0 | <2.0 | <2.0 | <2.0 |
| WATER | QS 100 | QS 100 | QS 100 | QS 100 | QS 100 | QS 100 | QS 100 | QS 100 | QS 100 | QS 100 | QS 100 | QS 100 | QS 100 |

*Formulations #7 to 13 are comparative formulas
**5% by weight aloe extract in water
***PRESERVATIVES (e.g., SODIUM BENZOATE, BENZOIC ACID), SALICYLIC ACID, CITRIC ACID, LECITHIN, TOCOPHEROL, ASCORBYL PALMITATE, HYDROGENATED PALM GLYCERIDES CITRATE, POTASSIUM SORBATE, FRAGRANCE Formulas above were prepared according to Table 1 and the following protocol: The polysaccharide (e.g., carrageenan) and polyol (e.g., glycerin) were combined in a side phase. The main phase was prepared with a cosmetically acceptable carrier such as water. Aloe Barbadensis leaf juice, if present, was added to the water. The cationic guar was then dispersed in the main phase with high shear. After hydration of the guar, the side phase was added into the main phase and the resulting mixture was heated to 70° C. Once the desired temperature was reached, the acids, preservatives, and other optional ingredients (additives) were added. Lastly, the surfactant(s) was added and the mixture was homogenized. The batch was then cooled to room temperature.

The final formulas had a pH within the range of 4-5; the pH was preferably set to 4.5.

Example 2

Testing on Hair

The formulations and their performance on hair swatches and/or on the hair of mannequin heads and/or on the hair on the heads of human volunteers were evaluated. The formulations were evaluated for visual appearance (translucency/opacity), consistency or texture (e.g., whether creamy or stringy or jello-like), foaming quality, and ease or difficulty with breaking or melting, wherein the ease of breaking/melting corresponds to the amount of force needed to break the gel structure and distribute on the hands and/or on hair. Their performance on hair was evaluated with respect to conditioning benefits such as wet detangling (when hair is wet) and smoothness of the hair (when wet or dry) and to ease of application or spreadability on the hair.

Example 2A

Comparative Evaluation on Hair Swatches
Protocol used to treat the hair swatch (1 gram bleached, caucasian hair)
1. Rinse swatch by running two (2) fingers through the hair thirty (10) times under water.
2. Treat swatch with respective formulation (2 gram) by distributing the product on the swatches using 2 fingers and running the fingers through the swatches 10 times. Then repeat step 1.
3. Comb swatch three times and leave to side to air dry.

TABLE 2

RESULTS
Scale: 1 = best/most, 6 = worst/least

| | #1 | #2 | #6 | #7 | #8 | #9 |
|---|---|---|---|---|---|---|
| Description | Invention | No Glyceryl oleate | 0.1% Glycerin | No Guar | 20% Glycerin | 3% Glyceryl Oleate |
| Attirbutes/Properties | | | | | | |
| Foaming | 3 | 2 | 1 | 5 | 4 | 6 |
| wet detangling | 2 | 3 | 4 | 5 | 6 | 1 |
| smoothness wet | 2 | 4 | 3 | 5 | 6, heavy drag | 1 |
| smoothness dry | 2 | 4 | 3 | 6 | 5 | 1 |
| Visual Comments | Translucent Good amount of foam | Translucent Good amount of foam quality | Translucent airy foam; good amount of foam | Translucet difficult to break | Opaque creamy low foam | Opaque no foam, creamy feel |

The table above shows that formulation #1 gave the best balance of foam and conditioning. Formulation #2, although less conditioning than Formulation #1, still gave satisfactory conditioning and easy distribution with good foam quality (good amount of foam). Formulation #6 provided more foam than Formulations #1 and #2 and it had an airy foam quality. Formulation #9 had the highest rating on conditioning effect, but it was opaque and had the lowest rating on foam amount and quality. Formulation #7 and #8 had overall, very low or the lowest scores with respect to all the attributes tested, including foam quality.

Formulations #1 and #2 were tested on mannequin heads and the results from each formula matched the results when they were tested on hair swatches.

Example 2B

In Vivo Testing

The inventive formulations were tested in vivo (on the hair of the heads of human volunteers/models in a salon) in comparison to a standard testing shampoo (DOP shampoo) mainly containing sodium laureth sulfate (sulfate-based anionic surfactant), coco-betaine, and water.

In Vivo Testing Results:

TABLE 3

| Rating by expert evaluators | |
|---|---|
| + | Slightly better |
| ++ | Noticeably better |
| = | equal to |
| − | Noticeably worse |

TABLE 4

N = 1 model

| | Formulation #2 | DOP |
|---|---|---|
| Distribution | + | |
| Foam | = | |
| Clean Feel | ++ | |
| Suppleness (wet with product) | ++ | |
| Conditioned | − | |
| Smoothness (wet with product) | ++ | |
| Smoothness (wet without product) | + | |
| Detangling | − | +++ |
| Discipline/shape (dry) | + | |
| Ease of drying | + | − |

TABLE 5

N = 2 models

| | Formulation #1 | DOP |
|---|---|---|
| Distribution | + | |
| Foam | = | |
| Clean Feel | | + |
| Suppleness (wet with product) | ++ | |
| Conditioned | ++ | |
| Smoothness (wet with product) | ++ | |
| Smoothness (wet without product) | + | |
| Detangling | ++ | |
| Discipline/shape (dry) | + | |
| Ease of drying | + | |

TABLE 6

N = 2 models

| | Formulation #5 | DOP |
|---|---|---|
| Distribution | = | |
| Foam | ++ | |
| Clean Feel | = | |
| Suppleness (wet with product) | = | |
| Conditioned | | ++ |
| Smoothness (wet with product) | ++ | |
| Smoothness (wet without product) | ++ | |
| Detangling | = | |
| Discipline/shape (dry) | + | |
| Ease of drying | = | |

For most of the attributes listed in Tables 4 to 6 above, the formulations of the invention performed better compared to the DOP shampoo on hair.

Example 2C

Evaluation of Nature of Anionic Surfactants

Protocol used to treat the hair swatch (1 gram bleached, caucasian hair)

1. Rinse swatch by running two (2) fingers through the hair thirty (10) times under water.
2. Treat swatch with respective formulation (2 gram) by distributing the product on the swatches using 2 fingers and running the fingers through the swatches 10 times. Then repeat step 1.
3. Comb swatch three times and leave to side to air dry.

TABLE 7

RESULTS:
RATING (1: BEST-3: WORST)

|  | Formulation #1 | Formulation #10 | Formulation #11 |
|---|---|---|---|
| Description | Contained total amount of 3.75% by weight DISODIUM LAURETH SULFOSUCCINATE (and) SODIUM LAURYL SULFOACETATE (Invention) | contained 2.7% by wt SODIUM LAURETH SULFATE | contained 20% by wt Glycerin with 2.7% by wt SODIUM LAURYL SULFATE |
| Application | 1 | 3 (difficult to break) | 2 |
| foaming | 3 | 1 | 2 |
| wet detangling | 2 | 3 | 1 |
| smoothness wet w/ product | 2 | 3 (feel fibers) | 1 |
| smoothness wet w/o product | 2 | 3 | 1 |
| Smoothness dry | 1 | 3 (feel ends) | 2 (feel ends) |
| Product Visual | Translucent | Translucent | Translucent |
| comments | Melts easily | Difficult to melt | Stringy consistency/ not a gel structure |

From the table above, it was evident that while formulation #1 had a lower rating on foaming than formulation #10 and #11, it was easy to apply on the hair, it had good conditioning properties and melted easily in the hand. On the other hand, formulation #10 performed less better with respect to conditioning properties and was difficult to melt, while formulation #11 had a stringy consistency which was not desirable (had a sticky consistency that was more liquid in form than a solid form in terms of structure and left a string-like residue when spread).

Example 2D

Evaluation of Amount of Anionic Surfactants

Protocol used to treat the hair swatch (1 gram bleached, caucasian hair)

1. Rinse swatch by running two (2) fingers through the hair thirty (10) times under water.
2. Treat swatch with respective formulation (2 gram) by distributing the product on the swatches using 2 fingers and running the fingers through the swatches 10 times. Then repeat step 1.
3. Comb swatch three times and leave to side to air dry.

TABLE 8

RESULTS:
RATING (1: BEST-3: WORST)

|  | Formulation #1 | Formulation #12 | Formulation #13 |
|---|---|---|---|
| Description | 3.75% BY WT DISODIUM LAURETH SULFOSUCCINATE (and) SODIUM LAURYL SULFOACETATE (Invention) | 1.25% BY WT DISODIUM LAURETH SULFOSUCCINATE (and) SODIUM LAURYL SULFOACETATE | 7.5% BY WT DISODIUM LAURETH SULFOSUCCINATE (and) SODIUM LAURYL SULFOACETATE |
| Application | 1 | 3 | 2 |
| Foaming | 2 | 3 | 1 |
| wet detangling | 2 | 1 | 3 |
| smoothness wet w/ product | 2 | 1 | 3 |
| smoothness wet w/o product | 1 | 2 | 3 |
| Smoothness dry | 2 | 3 | 1 |
| Product Visual | Jello-like (less rigid than Formulation #12) | Jello-like (more rigid) | Liquid thin (no jello) |
| comments | Easy melting |  | slimy |

The table above shows that when the total amount of the surfactants was much lower than the amount for formulation #1 as in formulation #13, the ratings for foaming, application on the hair and smoothness of the wet hair after rinsing and dry hair were worse compared to the ratings for formulation #1. In addition, while the detangling and smoothness ratings were higher when the hair was wet, the jello-like texture of the formula was more rigid. On the other hand, when the amount of the surfactant was much higher than the amount for formulation #1 as in formulation #12, it had better ratings for foaming and smoothness of dry hair compared to those for formulation #1. However, the ratings for all the other attributes were worse compared to those for formulation #1 and the texture of the formula was liquid thin and slimy to the touch.

Example 3

Comparison to a Commercial Product

TABLE 9

Comparative Commercial Formula Y (sold as a body wash)
US INCI NAME

Glycerin
*Eucalyptus* and Mint Infusion (*Eucalyptus Globulus* Leaf, *Mentha Piperita*)
Sodium Laureth Sulfate
Propylene Glycol
Carrageenan Extract (*Chondrus crispus*)
Fragrance
Cinnamon Leaf Oil (*Cinnamomum zeylanicum*)
Eugenol
Peppermint Oil (*Mentha piperita*)
Water (Aqua)
Cinnamal
Coumarin
Isoeugenol
Benzyl Benzoate
Limonene
Linalool
Red 4
Orange 4
Methylparaben
Propylparaben The comparative formula Y and Formulation #1 were applied onto the hair of a mannequin head in a half-head study (commercial product on the left side of the head and the inventive composition on the right side). The products were applied on the hair in order to simulate the cleansing/shampooing process in order to assess the foam and cleansing qualities with respect to foam abundance, foam stability (how long it lasts on the hair), wet detangling, wet smoothness and visual appearance of the product.

TABLE 10

RESULTS
Rating by expert evaluators: (1 to 5)
1 = low // 2.5 = average // 5 = high

|  | COMMERCIAL PRODUCT | Formulation #1 |
| --- | --- | --- |
| Flash Foam | 1 | 2.5 |
| Foam abundance | 1 | 3 |
| Foam stability | 1 | 2.5 |
| wet detangling | 2 | 3 |
| smoothness wet | 2 | 3 |
| Visual | Transparent | Translucent |
| comments | Very difficult to apply, product does not melt easily in hands | Good application, product melts easily in hands |
| Product type | body wash | Hair care |

FIG. 1 shows the amount of foam produced by the commercial product and formulation #1 on the hair of the mannequin head.

Formulation #1 distributed easier on hair than the commercial product. Foam amount and qualities were superior over the commercial product as well (more foam and more stable foam). In addition, hair felt smoother and softer and detangled better with Formulation #1.

It is to be understood that the foregoing describes preferred embodiments of the disclosure and that modifications may be made therein without departing from the spirit or scope of the disclosure as set forth in the claims.

What is claimed is:

1. A composition for treating keratinous substrates, the composition comprising:
   (a) at least one polysaccharide chosen from carrageenan and present in an amount of from about 1.5% to about 5% by weight, based on the total weight of the composition;
   (b) at least one cationic polymer present in an amount of at least 0.1% by weight based on the total weight of the composition;
   (c) at least one anionic surfactant chosen from sulfonate surfactants, carboxylic (carboxylate) surfactants, and mixtures thereof and present in an amount of from about 1.5% to about 10% by weight, based on the total weight of the composition;
   (d) at least one polyol; and
   (e) a cosmetically acceptable carrier; and
   wherein the sulfonate surfactants comprise sodium lauryl sulfoacetate and disodium laureth sulfosuccinate; and
   wherein the carboxylic (carboxylate) surfactants comprise sodium cocoyl glutamate and disodium cocoyl glutamate.

2. The composition according to claim 1, wherein the carrageenan is chosen from lamda carrageenan, kappa carrageenan, iota carrageenan, and mixtures thereof.

3. The composition according to claim 1, wherein the at least one cationic polymer is chosen from cationic cellulose derivatives, cationic gum derivatives, polymer derivatives of diallyldimethyl ammonium chloride, polymer derivatives of methacrylamidopropyltrimethylammonium chloride, and mixtures thereof.

4. The composition according to claim 3, wherein the at least one cationic polymer is chosen from polyquaternium-7, polyquaternium-10, guar hydroxypropyltrimonium chloride, and mixtures thereof.

5. The composition according to claim 4, wherein the at least one cationic polymer is guar hydroxypropyltrimonium chloride (also known as hydroxypropyl guar hydroxypropyltrimonium chloride).

6. The composition according to claim 1, wherein the amount of the at least one cationic polymer ranges from about 0.1% to about 10% by weight, based on the total weight of the composition.

7. The composition according to claim 1, wherein the amount of the at least one cationic polymer ranges from about 0.4% to about 2% by weight, based on the total weight of the composition.

8. The composition according to claim 1, wherein the composition is essentially free of sulfate surfactants.

9. The composition according to claim 1, wherein the at least one polyol is a compound containing at least two hydroxyl groups and containing from 2 to 8 carbon atoms, and wherein the at least one polyol is preferably chosen from ethylene glycol, propylene glycol, 1,3-butylene glycol, pentylene glycol, hexylene glycol, dipropylene glycol, glycerin, and mixtures thereof.

10. The composition according to claim 1, wherein the amount of the least one polyol ranges from about 0.1% to about 10% by weight, based on the total weight of the composition.

11. The composition according to claim 1, wherein the amount of the least one polyol ranges from about 1% to about 6% by weight, based on the total weight of the composition.

12. The composition according to claim 1, wherein the at least one consmetically acceptable carrier comprises water or a mixture of water and an organic solvent other than the at least one polyol (d).

13. The composition according to claim 1, further comprising a plant-based or fruit-based material.

14. The composition according to claim 1, further comprising at least one glyceryl ester chosen from glyceryl monoesters of C16-C22 saturated, unsaturated and branched chain fatty acids, and mixtures thereof.

15. The composition according to claim 14, wherein the least one glyceryl ester is chosen from glyceryl oleate, glyceryl monostearate (or glyceryl stearate), glyceryl distearate, glyceryl monoisostearate, glyceryl monopalmitate, glyceryl monobehenate, and mixtures thereof.

16. The composition according to claim 1, wherein the amount of the least one glyceryl ester ranges from about 0.05% to about 5% by weight, based on the total weight of the composition.

17. The composition according to claim 1, wherein the composition is translucent.

18. The composition according to claim 1, wherein the composition has a gel-like or semi-solid like appearance and/or texture.

19. The composition according to claim 1, wherein the keratinous substrates include hair.

20. The composition according to claim 1, wherein the composition is a shampoo or a cleansing or a conditioning shampoo composition.

21. A method for treating and/or cleansing a keratinous substrate, the method comprising contacting the keratinous substrate with a composition comprising the composition of claim 1.

22. The method according to claim 21, further comprising leaving the composition on the keratinous substrate for a period of time and then rinsing the keratinous substrate with water.

23. A translucent composition for cleansing hair, the composition comprising:
  (a) from about 1% to about 8% by weight of at least one polysaccharide chosen from carrageenan;
  (b) from about 0.2% to about 5% by weight of at least one cationic polymer chosen from cationic gum derivatives;
  (c) from about 1% to about 12% by weight of at least one anionic surfactant chosen from sulfonate surfactants, carboxylic (carboxylate) surfactants, and mixtures thereof;
  (d) from about 0.1% to about 8% by weight at least one polyol compound containing at least two hydroxyl groups and containing from 2 to 8 carbon atoms, and wherein the at least one polyol is preferably chosen from ethylene glycol, propylene glycol, 1,3-butylene glycol, pentylene glycol, hexylene glycol, dipropylene glycol, glycerin, and mixtures thereof;
  (e) a cosmetically acceptable carrier; and
  (f) optionally, from about 0.075% to about 4% by weight of at least one glyceryl ester chosen from glyceryl monoesters of C16-C22 saturated, unsaturated and branched chain fatty acids, and mixtures thereof;
  all weights being based on the total weight of the composition; and
wherein the sulfonate surfactants comprise sodium lauryl sulfoacetate and disodium laureth sulfosuccinate; and
wherein the carboxylic (carboxylate) surfactants comprise sodium cocoyl glutamate and disodium cocoyl glutamate.

24. A multi-component hair cosmetic agent for cleansing and conditioning hair, the hair cosmetic agent comprising:
  a) a first component comprising the composition of claim 1; and
  b) a second component comprising a conditioning composition;
wherein the first and second components are each packaged in a separate packaging assembly.

* * * * *